(12) United States Patent
Guo et al.

(10) Patent No.: US 7,264,776 B2
(45) Date of Patent: Sep. 4, 2007

(54) SANITARY AND COMPACT FECAL OCCULT BLOOD COLLECTOR

(76) Inventors: Huiyan Guo, 12678-22 Carmel Country Rd., San Diego, CA (US) 92130; Hsaioho Edward Tung, 4666 Cypress Glen Pl., San Diego, CA (US) 92130; Shaomin Sun, Acon Biotech Company, Ltd., #398 Tianmushan Road, Gudang Industrial Park, Hangzhou (CN) 310023; Yuchang Wu, Acon Biotech Company, Ltd., #398 Tianmushan Road, Gudang Industrial Park, Hangzhou (CN) 310023; Rong Yang, Acon Biotech Company, Ltd., #398 Tianmushan Road, Gudang Industrial Park, Hangzhou (CN) 310023; Yun Ling, Acon Biotech Company, Ltd., #398 Tianmushan Road, Gudang Industrial Park, Hangzhou (CN) 310023

( * ) Notice: Subject to any disclaimer, the term of this patent is extended or adjusted under 35 U.S.C. 154(b) by 154 days.

(21) Appl. No.: 10/890,541

(22) Filed: Jul. 12, 2004

(65) Prior Publication Data

US 2005/0009200 A1 Jan. 13, 2005

Related U.S. Application Data (60) Provisional application No. 60/486,374, filed on Jul. 11, 2003.

(51) Int. Cl.
*B01L 3/00* (2006.01)

(52) U.S. Cl. .............. 422/61; 422/55; 422/56; 422/58; 422/102; 436/63; 436/66; 436/174; 436/176

(58) Field of Classification Search .......... 422/56, 422/58, 61, 68.1, 79, 99, 100, 101, 102, 55; 436/63, 66, 161, 162, 174, 176, 177, 180
See application file for complete search history.

(56) References Cited

U.S. PATENT DOCUMENTS

| | | | | |
|---|---|---|---|---|
| 3,776,220 A | * | 12/1973 | Monaghan | .............. 600/572 |
| 4,014,748 A | * | 3/1977 | Spinner et al. | .............. 600/572 |
| 4,353,868 A | | 10/1982 | Joslin | |
| 4,473,079 A | | 9/1984 | Jasper | |
| 4,492,124 A | * | 1/1985 | Fleisher et al. | .......... 73/864.44 |
| 4,615,982 A | | 10/1986 | Lawrence | |
| 4,707,450 A | | 11/1987 | Nason | |
| 4,820,646 A | | 4/1989 | Lawrence | |
| 4,937,197 A | | 6/1990 | Lawrence | |
| 4,939,097 A | | 7/1990 | Lawrence | |
| 4,942,132 A | | 7/1990 | Lawrence | |
| 4,971,914 A | | 11/1990 | Lawrence | |
| 4,978,504 A | | 12/1990 | Nason | |
| 5,053,342 A | | 10/1991 | Lawrence | |

(Continued)

FOREIGN PATENT DOCUMENTS

EP 0727653 A2 8/1996

(Continued)

*Primary Examiner*—Jill Warden
*Assistant Examiner*—Dwayne K. Handy (57) ABSTRACT

A biological sample collection and test kit and a method of using the kit are disclosed in the application. The kit includes a swab, having a sample collection portion, a cover for covering the sample collection portion of the swab for hygienic purpose. Also disclosed is a package for the swab and the cover.

25 Claims, 6 Drawing Sheets

U.S. PATENT DOCUMENTS

| | | | |
|---|---|---|---|
| 5,064,766 A | 11/1991 | Wardlaw | |
| 5,068,197 A | 11/1991 | Lawrence | |
| 5,070,014 A | 12/1991 | Dorn | |
| 5,078,968 A | 1/1992 | Nason | |
| 5,081,040 A | 1/1992 | Patel | |
| 5,149,506 A | 9/1992 | Skiba | |
| 5,160,329 A * | 11/1992 | Oxley | 604/317 |
| 5,171,528 A | 12/1992 | Wardlaw | |
| 5,186,900 A * | 2/1993 | Jensen et al. | 422/104 |
| 5,192,501 A | 3/1993 | Guadangno | |
| 5,196,167 A | 3/1993 | Guadangno | |
| 5,217,874 A | 6/1993 | Guadangno | |
| 5,246,669 A | 9/1993 | Hayashi | |
| 5,264,181 A | 11/1993 | Schreiber | |
| 5,266,266 A * | 11/1993 | Nason | 422/58 |
| 5,279,964 A * | 1/1994 | Chrisope | 435/307.1 |
| 5,310,680 A | 5/1994 | Baker | |
| 5,331,973 A | 7/1994 | Fiedler | |
| 5,337,426 A | 8/1994 | Matusewicz | |
| 5,391,498 A | 2/1995 | Baker | |
| 5,403,741 A * | 4/1995 | Holbrook | 435/288.2 |
| 5,412,819 A | 5/1995 | Matusewicz | |
| 5,416,025 A | 5/1995 | Krepinsky | |
| 5,447,868 A | 9/1995 | Augurt | |
| 5,514,341 A | 5/1996 | Urata | |
| 5,543,115 A | 8/1996 | Karakawa | |
| 5,563,071 A | 10/1996 | Augurt | |
| 5,702,913 A | 12/1997 | Guadangno | |
| 5,882,942 A | 3/1999 | Kagaya | |
| 5,948,687 A | 9/1999 | Cleator | |
| 6,057,166 A | 5/2000 | Childs | |
| 6,171,259 B1 * | 1/2001 | Fisher | 600/549 |
| 6,180,395 B1 * | 1/2001 | Skiffington et al. | 435/287.6 |
| 6,207,113 B1 | 3/2001 | Kagaya | |
| 6,221,678 B1 | 4/2001 | Chandler | |
| 6,248,294 B1 * | 6/2001 | Nason | 422/58 |
| 6,268,136 B1 | 7/2001 | Shuber | |
| 6,271,046 B1 | 8/2001 | Chandler | |
| 6,291,171 B1 * | 9/2001 | Ricciardi et al. | 435/6 |
| 6,410,336 B1 | 6/2002 | Augurt | |
| 6,539,817 B2 * | 4/2003 | Kozak et al. | 73/864.91 |
| 6,565,808 B2 * | 5/2003 | Hudak et al. | 422/58 |
| 2001/0004532 A1 | 6/2001 | Chandler | |
| 2004/0019295 A1 | 1/2004 | Zhou | |
| 2004/0019298 A1 | 1/2004 | Zhou | |
| 2004/0184996 A1 | 9/2004 | Rabinowitz | |
| 2005/0036910 A1 | 2/2005 | Zhou | |
| 2005/0158869 A1 | 7/2005 | Chandler | |
| 2005/0158878 A9 | 7/2005 | Chandler | |

FOREIGN PATENT DOCUMENTS

| | | |
|---|---|---|
| EP | 0727653 B1 | 8/1996 |
| EP | 1384442 A1 | 1/2004 |
| JP | 200258308 | 10/1990 |
| JP | 05093722 A2 | 4/1993 |
| JP | 07012808 A | 1/1995 |
| JP | 11295194 A2 | 10/1999 |
| JP | 07049344 A | 2/2005 |
| WO | WO90/13802 A1 | 11/1990 |
| WO | WO92/11536 A1 | 7/1992 |
| WO | WO93/05387 A1 | 3/1993 |
| WO | WO94/22017 A1 | 9/1994 |
| WO | WO95/08120 A1 | 3/1995 |
| WO | WO99/18436 | 4/1999 |
| WO | WO99/56103 A1 | 11/1999 |
| WO | WO00/10008 A1 | 2/2000 |
| WO | WO00/54029 A1 | 9/2000 |

* cited by examiner

FIG.6A

SANITARY AND COMPACT FECAL OCCULT BLOOD COLLECTOR

CROSS-REFERENCE TO A RELATED APPLICATION

This application claims priority of previously filed U.S. Provisional Patent Application Ser. No. 60/486,374 filed Jul. 11, 2003. The disclosure of the provisional application is incorporated herein by reference.

BACKGROUND OF THE INVENTION

1. Field of the Invention

The present invention relates generally to the field of fecal sample collection devices, which can be used to manipulate samples, including samples used to assay for indicators of medical condition. In particular, the present invention relates to improvements in fecal collection device design that provide increased ease of use to the subject and the technician, as well as increased cleanliness, decreased incidence of sample contamination and reduced repulsiveness of the sample.

2. Description of the Related Art

Specimen test slides and procedures for detecting occult blood in fetal matter are well known. For example, U.S. Pat. No. 3,996,006 discloses slides having a specimen receiving sheet between a front panel and a rear panel with openings in the front and rear panels and pivotal covers or flaps to cover these openings. One such test slide is sold under the trademark of "Hemoccult".

The specimen receiving sheet is generally an absorbent paper impregnated with a guaiac reagent. The hemoglobin catalyzed oxidation of the guaiac extract coated paper is used clinically to detect occult blood in feces.

A sample of fecal matter is smeared onto the guaiac paper through an opening of the front panel. The panel is then covered and the flap of the rear panel is opened. A developing solution such as hydrogen peroxide is applied to the guaiac paper via the corresponding opening in the rear panel. If blood is present in the fecal matter, the guaiac reaction will color the paper blue.

One of the problems associated with this test is the number of false negatives, i.e., negative test results in samples of known bleeding patients. The test is not sensitive enough to pick up power levels of blood in the feces.

Previous attempts have been made to increase the sensitivity of the test result. For example, the patient collects the specimen and posts the specimen to the doctor, hospital or laboratory for test. However, since the design or package is not good enough, the specimen is easily disabled when the doctor, hospital or laboratory receives it. Furthermore, previous design does not have sanitary means so as not to stain the patient or the doctor, or the laboratory assistant.

It is therefore the object of this invention to provide a sanitary collection and package means.

SUMMARY

The present invention includes a variety of other useful aspects, which are detailed herein. These aspects of the invention can be achieved by using the articles of manufacture and compositions of matter described herein. To gain a full appreciation of the scope of the present invention, it will be further recognized that various aspects of the present invention can be combined to make desirable embodiments of the invention. In addition, a variety of other aspects and embodiments of the present invention are described herein.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as "up" and "down" or "upper" or "lower" and the like refer to orientation of the parts during use of the device. Where a term is provided in the singular, the inventors also contemplate the plural of that term. The nomenclature used herein and the laboratory procedures described below are those well known and commonly employed in the art. As employed throughout the disclosure, the following terms, unless other wise indicated, shall be understood to have the following meanings:

"Repulsiveness" denotes the quality of being disgusting, revolting, repulsive, or the like. For example, fecal samples are generally considered disgusting by testing laboratory technicians, for reasons such as the fact that the sample comprises excrement and the sample has an objectionable smell. In the art of biological sample testing, this quality is some time referred to as "the ick factor."

"Assaying" denotes testing for or detecting the presence of a substance or material, such as, but not limited to, a chemical, an organic compound, an inorganic compound, a metabolic product, a drug or a drug metabolite, an organism or a metabolite of such an organism, a nucleic acid, a protein, or a combination thereof. Optionally, assaying denotes measuring the amount of the substance or material. Assaying further denotes an immunological test, a chemical test, an enzymatic test, and the like.

An element of the present invention is "integral to" another element of the present invention when the two elements are manufactured as a single piece.

An element of the present invention is "separate from" another element of the present invention when the two elements are manufactured as separate pieces.

A "reagent" can be any chemical, including organic compounds and inorganic compounds and combinations thereof. A reagent can be provided in gaseous, solid, or liquid form, or any combination thereof, and can be a component of a solution or suspension. A reagent preferably includes fluids, such as buffers useful in methods of detecting analytes in a sample or specimen, such as anticoagulants, diluents, buffers, assay reagents, specific binding members, detectable labels, enzymes and the like. A reagent can also include an extractant, such as a buffer or chemical, to extract an analyte from a sample or specimen or a sample collection device. For example, a buffer can be used to extract analytes from the sample or specimen, such as LPS from bacteria.

An "analysis device" or "assay device" is a device for analyzing a sample or specimen. An analysis device can be used to detect the presence and/or concentration of an analyte in a sample or specimen, or to determine the presence and/or numbers of one or more components of a sample or specimen, or to make a qualitative assessment of a sample or specimen. Analysis devices of the present invention include but are not limited to cuvettes, slides, lateral flow detection devices such as assay strip devices, and columns.

A "lateral flow detection device" or a "lateral flow test device" is a device that determines the presence and/or amount of an analyte in a liquid sample or specimen as the liquid sample or specimen moves through a matrix or material by lateral flow or capillary action, such as an immunochromatographic device. A lateral flow detection device may be used in a substantially vertical or a substantially horizontal orientation or in an orientation substantially between vertical and horizontal. Persons knowledgeable in the art commonly refer to a lateral flow detection device using terms such as "immunochromatographic," "dip sticks," "membrane technology" and "test strips."

"Analyte" is the compound or composition to be measured that is capable of binding specifically to a ligand, receptor, or enzyme, usually and antibody or antigen such as a protein or drug, or a metabolite, the precise nature of antigenic and drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference. Analytes can include antibodies and receptors, including active fragments or fragments thereof. An analyte can include and analyte analogue, which is a derivative of an analyte, such as, for example, an analyte altered by chemical or biological methods, such as by the action of reactive chemicals, such as adulterants or enzymatic activity. An analyte may be a drug or drug metabolite, especially, but not limited to drugs of abuse, such as, for example amphetamines (speed), cocaine, THC (cannabis/pot), opiates (heroine), phencyclidine (PCP), methadone, benzodiazepines, methamphetamines (MDMA/ecstasy), phencyclidine (PCP/angle dust), tricyclic antidepressants and barbiturates.

An "antibody" is an immunoglobulin, or derivative or fragment or active fragment thereof, having an area on the surface or in a cavity, which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

"Sample" or "specimen" may be used interchangeably. "Sample" or "specimen" denotes any material to be assayed for the presence and/or concentration of an analyte in a sample or specimen, or to determine the presence and/or numbers of one or more components of a sample or specimen, or to make a qualitative assessment of a sample or specimen. A sample can be the same as a specimen. Preferably, a sample is a fluid sample, preferably a liquid sample. Examples of liquid samples that may be assayed using a assay device of the present invention include bodily fluids including blood, serum, plasma, saliva, urine, ocular fluid, semen, and spinal fluid; water samples, such as samples of water from oceans, seas, lakes, rivers, and the like, or samples from home, municipal, or industrial water sources, runoff water or sewage samples; and food samples, such as milk or wine. Viscous liquid, semi-solid, or solid specimens may be used to create liquid solutions, eluates, suspensions, or extracts that can be samples. For example, throat or genital swabs may be suspended in a liquid solution to make a sample. Samples can include a combination of liquids, solids, gasses, or any combination thereof, as, for example a suspension of cells in a buffer or solution. Samples can comprise biological materials, such as cells, microbes, organelles, and biochemical complexes. Liquid samples can be made from solid, semisolid or highly viscous materials, such as soils, fecal matter, tissues, organs, biological fluids or other samples that are not fluid in nature. For example, these solid or semi-solid samples can be mixed with an appropriate solution, such as a buffer, such as a diluent or extraction buffer. The sample can be macerated, frozen and thawed, or otherwise extracted to form a fluid sample. Residual particulates can be removed or reduced using conventional methods, such as filtration or centrifugation.

A "control" is a portion of the assay designed to determine various aspects of progress of the assay conducted on a sample of a subject. For example, one might want to determine if the assay ran correctly, if the assay gave a correct answer, if the assay is complete, and the like. In some cases, a control is designed to provide an example of a positive or negative result, to which the person running the assay can compare the results obtained from assaying the sample of the subject. Controls may be run in various ways, which are well known in the art, depending upon the purpose of the control. For example, procedural controls generally indicate that the assay is complete. More specifically, in an immunoassay test strip, a control line may appear at the end of the test zone, to indicate that the sample has run far enough in the test strip and that the assay has been conducted for a long enough time. In another example, "reactive controls" may be run. Reactive controls may comprise extra lines on the test strip that mimic what the test result lines would look like if the test is either positive or negative, depending upon if the reactive control is either a positive or negative reactive control line. Generally, reactive controls are not considered to be true positive or negative controls. In yet another example, controls may be positive or negative. In the art, they may be referred to as true positive or true negative controls, in order to differentiate this type of control from the procedural or reactive controls. In the example of true positive and negative controls, two extra test strips are used, in addition to the test strip used to assay the subject sample. Positive and negative control solutions are also provided to the user. The positive control solution is similar to the sample solution and is spiked with a defined amount of the analyte of interest, or an analogue thereof, for which the subject sample will be assayed. The positive control solution will be applied to one of the test strips and will react with the appropriate reagents on the test strip to produce a positive test result. The negative control solution is substantially the same as the positive control, except that the negative control solution is not spiked with the analyte of interest. The negative control solution is applied to a second test strip. The negative control solution produces a negative result. The subject sample would be applied to the third test strip, in parallel with the positive and negative controls being applied to their respective test strips as described above. At the conclusion of the assay, the assay results of the subject sample could be compared to the assay results of the positive and negative tests, to confirm the positive or negative results of the assay of the subject sample.

Other technical terms used herein have their ordinary meaning in the art that they are used, as exemplified by a variety of technical dictionaries.

Sample Collection Device

The problem of collecting biological samples from a subject, especially fecal samples, is that the samples are considered disgusting by the subject and the laboratory technician. Because of this repulsive quality, may subject have difficulty collecting their own samples and laboratory technicians may avoid working with the samples. The present invention overcomes this long term problem by providing an easier, cleaner and quicker device for collecting the sample and providing the sample to the laboratory technician.

A related issue is the high cost of manufacturing and mailing most fecal occult blood collectors. The devices of the prior art tend to be bulky, which requires more materials to manufacture and ship to the customer, and consequently significant expense to the end user. The prior art devices are difficult for the subject to use in the home setting. In addition, it is expensive for the patient to mail the device with the collected samples to the testing laboratory.

PREFERRED EMBODIMENTS OF THE INVENTION

Figure 1A:
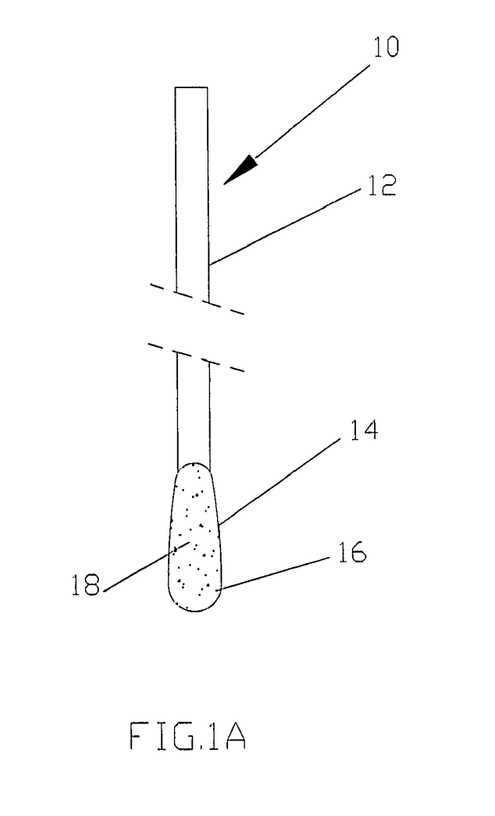
FIG. 1A depicts a portion of one embodiment of the present invention, a swab for collecting the sample.
Figure 1B:
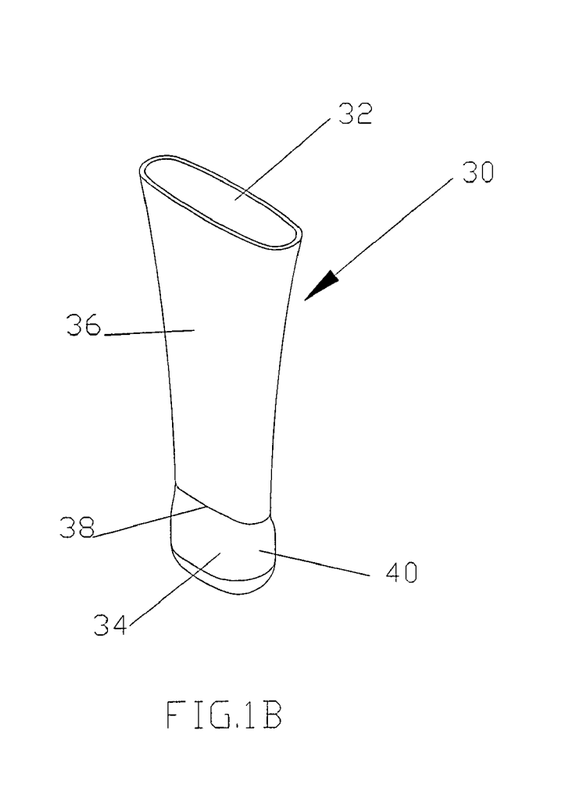
FIG. 1B depicts another portion of one embodiment of the present invention, a cover for the absorbent end of the swab.

FIG. 1A illustrates a swab 10 and FIG. 1B illustrates a cover 30 engageable with the swab 10. The swab 10 includes a slim stick handle 12 and a header 14 at an end of the stick handle 12. The stick handle 12 may be made of plastic, wood, bamboo, metal, or paper, or any other available material that has some stiffness, and may have any convenient length and cross-section, although a cylindrical handle is preferred. The stick handle 12 may be hollow if made of plastic or metal to save material. The header 14 is configured or constructed to adhere and hold the specimen of a person or animal who requires an assay. The header 14 has an enlarged portion 16 whose size is larger in somewhat than that of at least a section of the stick handle 12. In a preferred embodiment of the present invention, the header 14 has a liquid-pervious material 18 wound on the end of the stick handle 12 for adhering and holding the specimen, especially the liquid specimen. The liquid-pervious material 18 may be spun cotton, cotton fiber, sponge and any other material capable of adhering and holding specimen. In an alternate preferred embodiment of the present invention, the header 14 defines some grooves (not shown) on the outer surface thereof such that the specimen, especially the solid specimen may be adhered and held in the grooves for testing. In another preferred embodiment of the present invention, the header 14 may have brush or hair (not shown) thereon for adhering and holding the specimen. U.S. Pat. No. 5,514,341, issued to Urata et al. on May 7, 1996 and U.S. Pat. No. 5,882,942 issued to Kagaya on Mar. 16, 1999 discloses such headers, which are incorporated herein by reference.

Figure 1C:
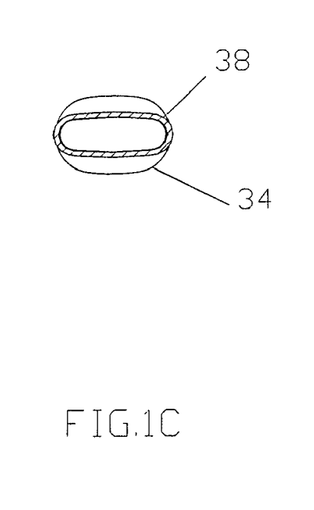
FIG. 1C shows a cross-section of the cover taken along a throat of the cover designated by the label 38.
Figure 2A:
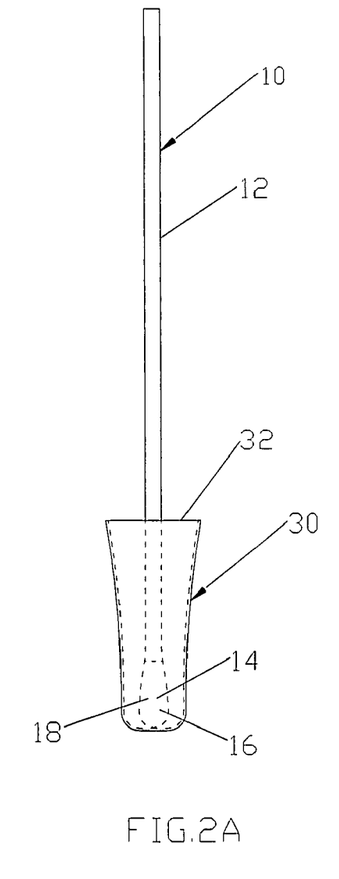
FIGS. 2A–2C depict the swab partially covered by the cover in different perspectives.
Figure 2B:
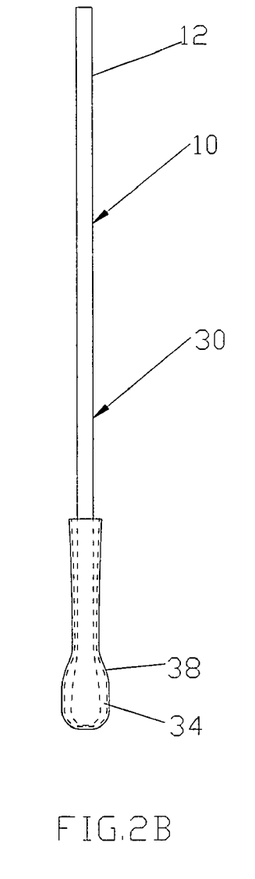
Figure 2C:
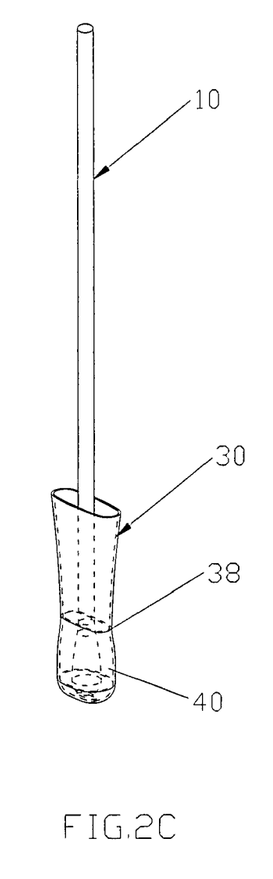

The cover 30 is somewhat deformable or elastic and has only one opening 32 at a top portion thereof such that the header 14 of the stick handle 10 may be inserted into and withdrew from the cover 30 through the opening 32. The cover 30 has a hollow bump 34 at a lower portion thereof and a sleeve 36 above the hollow bump 34. The sleeve 36 has a larger size at the area away from the hollow bump 34 than the area adjacent the hollow bump 34 such that a throat 38 is formed at the conjunction area of the hollow bump 34 and the sleeve 36. The hollow bump 34 defines a chamber 40 therein. When the header 14 is passing through the throat 38 of the cover 30, the enlarged portion 16 will elastically expand the throat 38 since the throat 38 has a smaller dimension than the enlarged portion 16 in at least one direction. After enter the chamber 40 of the hollow bump 34, the header 14 is not compressed by the cover 30 since the chamber 40 provides a loose space for the enlarged portion 16. However, the throat 38 will keep the header 14 in the chamber 40, unless the stick handle 10 is roughly withdrew from the cover 30. In a preferred embodiment of the present invention, the cover 30 is oblate so that the package of the covers 30 is more compact. The word "oblate" means that the cover 30 has a larger dimension in one direction than a perpendicular direction in a cross-section thereof (as shown in FIG. 1B). As clearly shown in FIG. 1C, to facilitate the insertion of the header 34 into the chamber 40, the throat 38 is preferred to be oblate, so that the throat 38 is much flexible. FIGS. 2A–2C show that the header 34 is adequately accommodated into the chamber 40 of the cover 30.

Figures 3A, 3B:
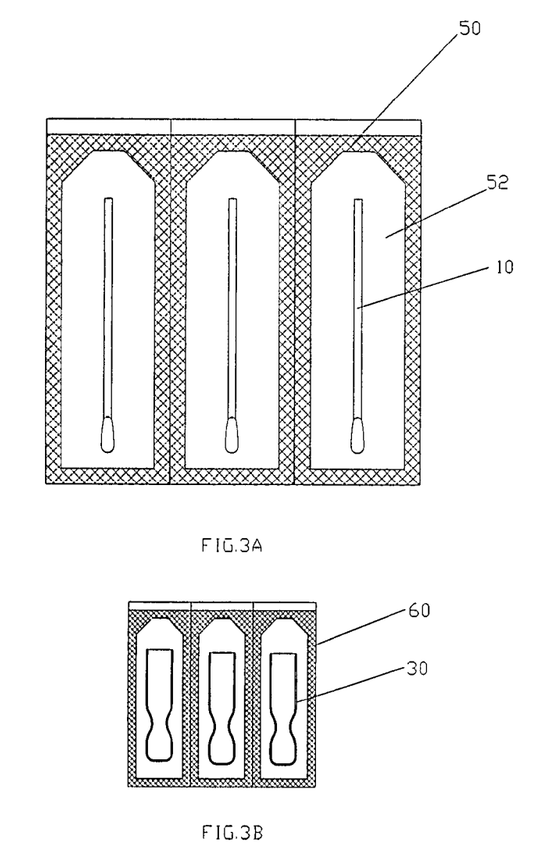
FIGS. 3A–3C depict packages for the swabs and the covers.
Figure 3C:
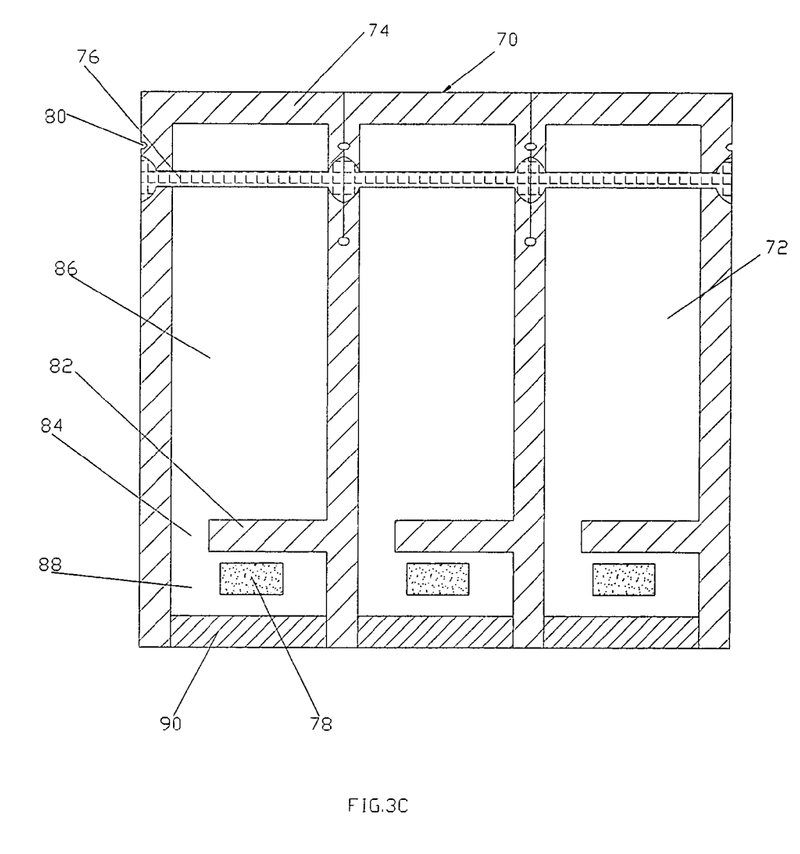

FIGS. 3A–3C illustrate how the stick handles 10 and the covers 30 may be packaged. As shown in FIG. 3A, three swabs 10 are respectively packaged in three chambers 52 of a first tear-away wrapper 50 side by side. As shown in FIG. 3B, three covers 30 are also packaged in a second tear-away wrapper 60 just like the swabs 10. However, each swab 10 can be packaged together with each cover 30 in a single chamber 52, or the swabs 10 or the covers 30 can be packaged in a single chamber 52, or the swabs 10 and the covers 30 can be packaged in a single chamber 52. The wrappers 50, 60 are preferably made of transparent foil or plastic material for inspecting the swabs 10. However, the wrappers 50, 60 can also be made of any other materials that are air-tight and liquid-tight.

Referring to FIG. 3C, a sealable bag-like container 70 that generally includes three bags 72 is adapted to receive the swabs 10 with stool sample on the headers 14 that are covered by the covers 30 (as illustrated below in detail). The container 70 is preferably made of foil material so as to protect the stool sample during shipping. However, any other nontransparent and air-tight and liquid-tight material can be used as long as the stool sample in the container 70 is still usable for the test in a predetermined period. Each bag 72 has a desiccant 78 therein for drying out the stool sample absorbed on the header 14 of the swab 10. Each bag 72 has a sealed margin 74 and a zip-lock-like mechanism 76 adjacent the sealed margin 74 such that after the sealed margin 74 is torn away, the zip-lock like mechanism 76 still remains the bag 72 in air-tight and liquid-tight. The sealed margin 74 defines a V-cut 80 for facilitating the removal thereof. In a preferred embodiment of the present invention, the bag 72 has a septum 82 adjacent a bottom thereof such that the bag 72 is divided into a first room 86 for receiving the swab 10 and a second room 88 for receiving the desiccant 78. The bag 72 still leaves a channel 84 communicating the first and the second rooms 86 and 88 so that the desiccant 78 can dry out the stool sample on the header 14 of the swab 10. The bottom margin 90 is sealed after the desiccant 78 is received in the second room 88. However, the bag 72 may not have the septum 82.

Figure 4A:
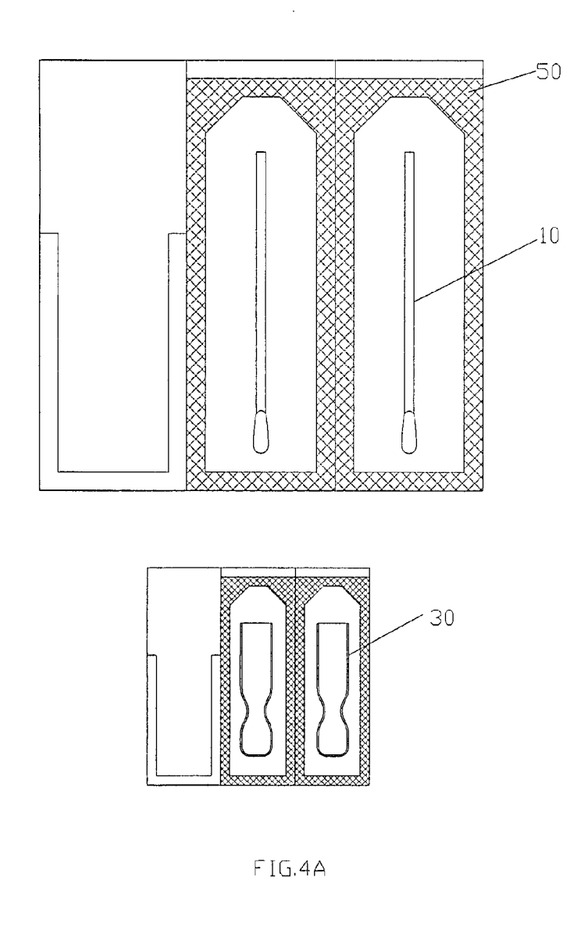
FIGS. 4A–4C depict how the swabs and the covers are used.
Figure 4B:
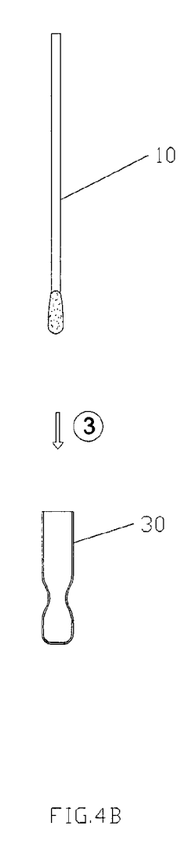
Figure 4C:
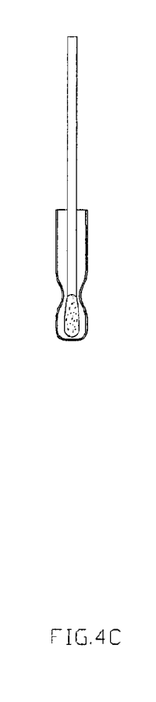

Now, it will illustrate how the kit works. Referring to FIGS. 4A–4C, the first wrapper 50 is torn and the swab 10 is taken out to have stool sample on the header 14 thereof. The cover 30 is taken out from the second wrapper 60 to have the header 14 of the swab 10 received in the hollow bump 34 of the cover 30. When passing through the throat 38 of the cover 30, the throat 38 will be expanded a little, and will recover to the original shape after the header 14 is adequately received in the hollow bump 34. The throat 38 will keep the header 14 in the hollow bump 34, as is shown in FIG. 4C.

Figure 5A:
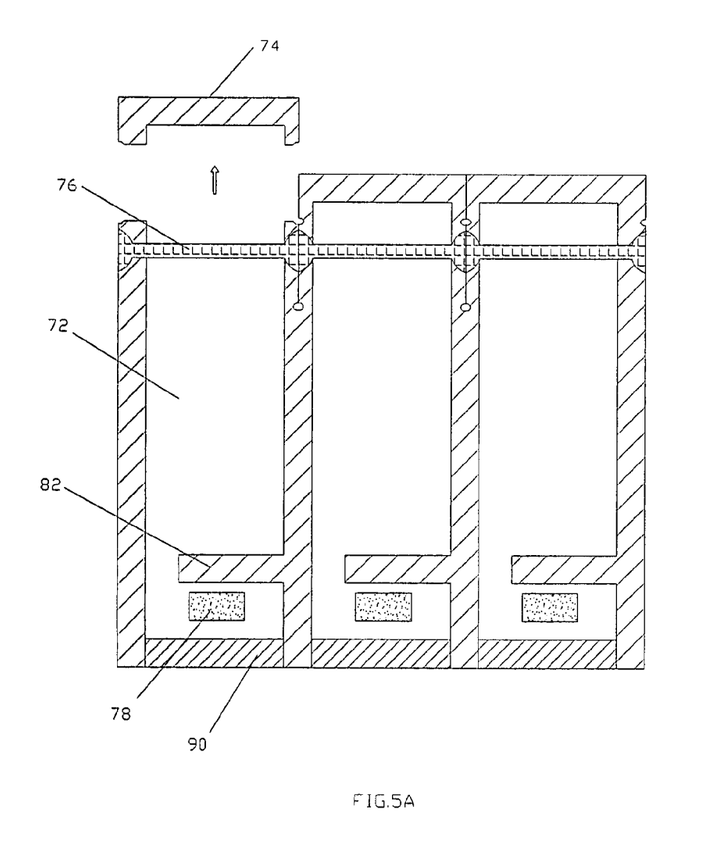
FIGS. 5A–5B depict how the covered swabs are packaged.
Figure 5B:
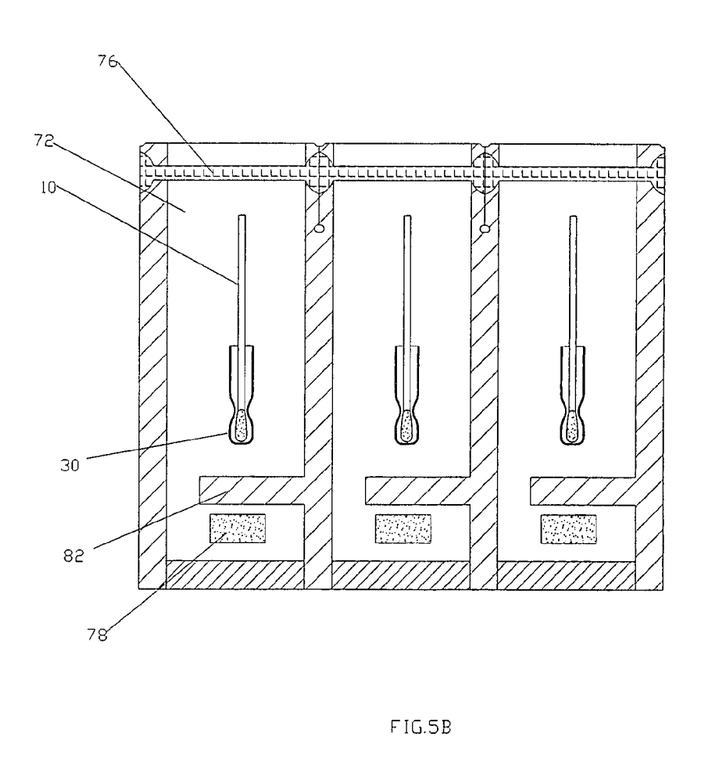

Referring to FIGS. 5A and 5B, the sealed margin 74 is removed so as to open the zip-lock like mechanism 76. The swab 10 with the cover 30 on the header 14 thereof is put into the bag 72, and then the zip-lock like mechanism 76 is closed so that the desiccant 78 will dry out the stool sample. After the three bags 72 are filled with the swabs 10 and the zip-lock like mechanism 76 are closed as illustrated in FIG. 5B, the kit is enclosed in an envelope with name and address thereon. The envelope is posted to the doctor, hospital or laboratory for test. Since the envelope is conventional, it is not illustrated here in detail for concision.

Figure 6A:
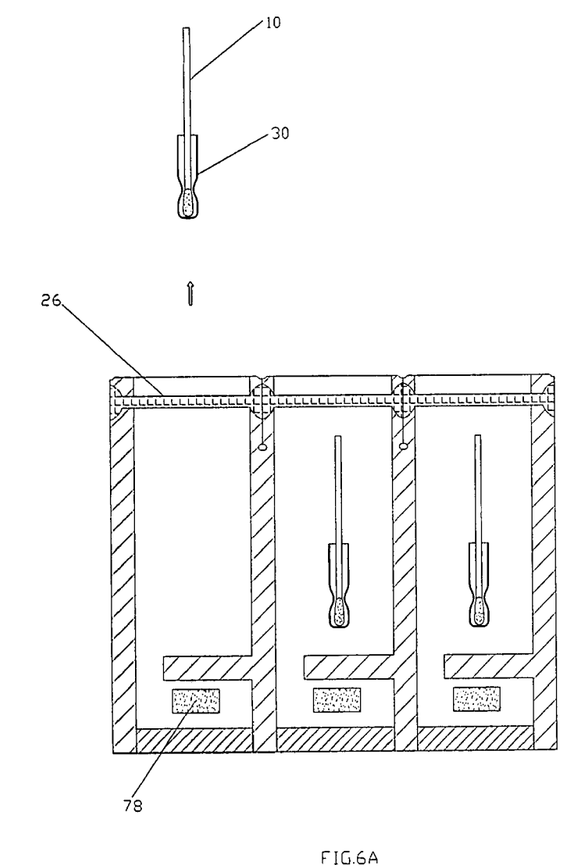
FIGS. 6A–6B depict how the covered swabs are taken out from the package for test.
Figure 6B:
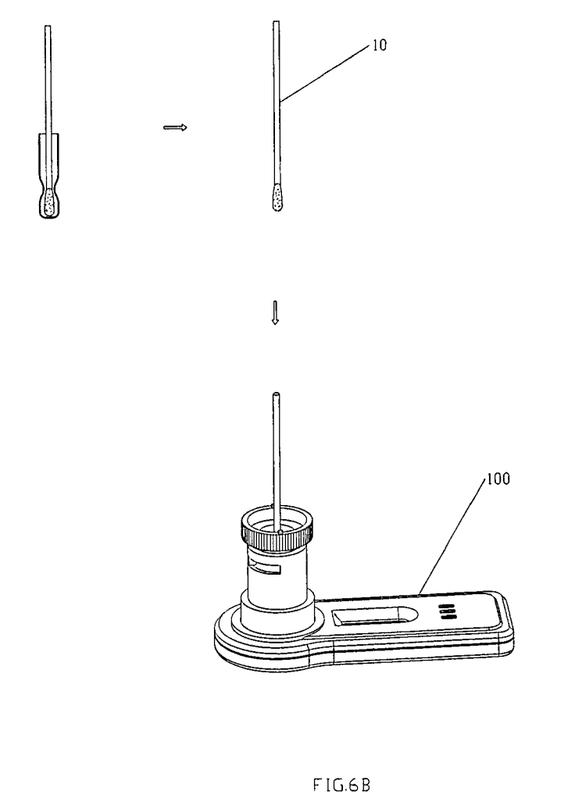

Referring to FIGS. 6A and 6B, when the doctor or the lab assistant receives the envelope, the kit is taken out and the zip-lock like mechanism 76 is opened to take out the swab 10 with the cover 30 on the header 14. The cover 30 is then removed from the swab 10 and the header 14 of the swab 10 is inserted into a test device 100. The test device 100 includes a test strip (not shown in the drawings), which has elements therein for detecting the components in the stool sample as clinical data. A buffer or sample diluent is added into the test device 100 so as to dissolve the stool sample. The buffer or sample diluent with the stool sample will flow to the test strip and the test result can be read out by inspecting the color change of the test strip. The test device 100 and the test strip are well know in the HEALTHCARE QUICK DIAGNOSTIC TEST technical field, and LATERAL FLOW is one of the most popular technology of this technical field. U.S. Pat. No. 6,391,652 B2, issued to Okada et al. on May 21, 2002 and U.S. patent application publication No. US 2003/0119203A1, published on Jan. 26, 2003 disclose a test strip. U.S. Pat. No. 6,528,325, issued to Hubscher et al. on Mar. 4, 2003 discloses one type of such a device. These references are incorporated herein by reference. A variety of test devices could be used to analyze the samples. For example, a sample extracting immunoassay cassette, similar to the device disclosed in U.S. Pat. No. 6,565,808, might be used.

The embodiments described and the alternative embodiments presented in the figures and in the detailed description of the drawings are intended as examples rather than as limitations. Thus, the description of the invention is not intended to limit the invention to the particular embodiments disclosed but it is intended to encompass all equivalents and subject matter within the spirit and scope of the invention as described above and as claimed in the claims which follow.

EXAMPLE

A patient has come to the doctor because he has had tary stools. The doctor suspects that the patient may have colon cancer. To assist in diagnosis, the doctor sends the patient home with the feces collector of the present invention. At home, on three different days, the patient collects his stool. He removes the cover from a swab, touches the swab to the stool, to collect a small sample, and replaces the cover on the swab. The patient then places the swab in one of the chambers of the divided collection bag and zips the bag closed. When all three samples have been collected, the patient puts the bag containing the used swabs in the provided mailing envelope and places the envelope in the mail. When the samples arrive at the testing laboratory, a technician removes each swab, individually, and uses it to test the collected sample for the presence of occult blood. The results of the tests will be reported to the doctor, who will then determine the next course of action for the patient.

We claim:

1. A sample collection device for collecting biological samples of a subject in need thereof, comprising:
   a swab including a sample collection portion adapted to contact a sample;
   a swab cover having a throat and used to cover at least the sample collection portion of the swab;
   a sealable container used to hold said swab and swab cover and having at least one bag comprising
   a first room; and
   a second room partially isolated from the first room by a septum and communicated with the first room via a channel; and
   a desiccant disposed in the second room for drying the swab after the swab has contacted the sample.

2. The sample collection device of claim 1 wherein the sealable container further comprises a sealed margin that is able to be torn away.

3. The sample collection device of claim 1, wherein the sample collection portion of the swab includes liquid-pervious material.

4. The sample collection device of claim 3 wherein the liquid-pervious material is cotton fiber material.

5. The sample collection device of claim 1 wherein the swab has an enlarged portion at the sample collection area that is larger than an other portion thereof.

6. The sample collection device of claim 1 wherein the swab cover includes a closed hollow bump with a chamber defined in the hollow bump, and wherein the sample collection portion of the swab has a dimension smaller than the hollow bump but larger than the throat.

7. The sample collection device of claim 1 wherein the swab cover includes a sleeve connected with the throat and defining an opening for facilitating the entrance of the sample connection portion of the swab.

8. The sample collection device of claim 1 wherein the swab cover is made of deformable or elastic material.

9. The sample collection device of claim 1 wherein the swab cover is oblate.

10. The sample collection device of claim 1 wherein the swab cover is made of transparent or semitransparent material.

11. The sample collection device of claim 1 wherein the sealable container is made of foil or plastic material.

12. The sample collection device of claim 1 wherein the bag has a zip-lock like mechanism adjacent the sealed margin so that the bag can still be closed after the sealed margin is torn away.

13. The sample collection device of claim 1 wherein the swab and the swab cover are not packaged in the sealable container before the swab contacts with the biological sample.

14. A kit for collecting and testing biological samples of a subject in need thereof, comprising:
   a swab including a sample collection portion adapted to contact a sample;

a swab cover having a throat and used to cover at least the sample collection portion of the swab;

a sealable container used to hold the swab and the swab cover, and having at least one bag including a first room and a second room partially isolated by a septum, the first room and second room communicated via a channel;

a desiccant disposed in the second room for drying the swab after the swab has contacted the sample; and a test device including colored bodies and antigens or antibodies therein, the colored bodies being isolated from the antigens or antibodies before test, but the colored bodies being able to combine with the antigens or antibodies when the dissolved biological samples of a subject flow through the test device in case of the biological samples including the assay elements that are able to combine with the antigens or antibodies in the test device.

15. The kit of claim 14 wherein the sample collection portion of the swab includes liquid-pervious material.

16. The kit of claim 15 wherein the liquid-pervious material is cotton fiber material.

17. The kit of claim 14 wherein the swab has an enlarged portion at the sample collection area that is larger than an other portion thereof.

18. The kit of claim 14 wherein the swab cover includes a closed hollow bump with a chamber defined in the hollow bump, and wherein the sample collection portion of the swab has a dimension smaller than the hollow bump but larger than the throat.

19. The kit of claim 14 wherein the swab cover includes a sleeve connected with the throat and defining an opening for facilitating the entrance of the sample connection portion of the swab.

20. The kit of claim 14 wherein the swab cover is made of deformable or elastic material.

21. The kit of claim 14 wherein the swab cover is oblate.

22. The kit of claim 14 wherein the swab cover is made of transparent or semitransparent material.

23. The kit of claim 14 wherein the sealable container is made of foil or plastic material.

24. The kit of claim 14 wherein the bag has a zip-lock like mechanism adjacent the sealed margin so that the bag can still be closed after the sealed margin is torn away.

25. The kit of claim 14 wherein the swab and the swab cover are not packaged in the sealable container before the swab contacts with the biological sample.

* * * * *